(12) United States Patent
Peake

(10) Patent No.: US 12,728,218 B2
(45) Date of Patent: Sep. 8, 2026

(54) SYSTEMS AND METHODS FOR DETERMINING A REMAINING USEFUL LIFE OF AN INTERFACE OF A RESPIRATORY THERAPY SYSTEM

(71) Applicant: ResMed Inc., San Diego, CA (US)

(72) Inventor: Gregory Robert Peake, Sydney (AU)

(73) Assignee: ResMed Inc., San Diego, CA (US)

( * ) Notice: Subject to any disclaimer, the term of this patent is extended or adjusted under 35 U.S.C. 154(b) by 719 days.

(21) Appl. No.: 18/306,007

(22) Filed: Apr. 24, 2023

(65) Prior Publication Data

US 2023/0338677 A1 Oct. 26, 2023

Related U.S. Application Data

(60) Provisional application No. 63/334,528, filed on Apr. 25, 2022.

(51) Int. Cl.
*A61M 16/06* (2006.01)
*A61M 16/00* (2006.01)

(52) U.S. Cl.
CPC ...... *A61M 16/0051* (2013.01); *A61M 16/024* (2017.08); *A61M 16/06* (2013.01); *A61M 2205/52* (2013.01); *A61M 2205/581* (2013.01)

(58) Field of Classification Search
CPC ............ A61M 16/0051; A61M 16/024; A61M 16/06; A61M 16/0683; A61M 16/0816; A61M 16/0875; A61M 2205/52; A61M 2205/581; A61M 2205/3375; A61M 2202/0225; A61M 16/00; A61M 2210/0618; A61M 2210/0625
See application file for complete search history.

(56) References Cited

U.S. PATENT DOCUMENTS 5,245,995 A 9/1993 Sullivan et al.
6,502,572 B1 1/2003 Berthon-Jones et al.
(Continued)

FOREIGN PATENT DOCUMENTS

WO 2008/138040 A1 11/2008
WO 2012/012835 A2 2/2012
(Continued)

OTHER PUBLICATIONS

Ayappa et al., "Non-Invasive Detection of Respiratory Effort-Related Arousals (RERAs) by a Nasal Cannula/Pressure Transducer System", NYU School of Medicine; published in Sleep, vol. 23, No. 6, 2000, pp. 763-771.

*Primary Examiner* — Bradley H Philips
*Assistant Examiner* — Tyler A Raubenstraw
(74) *Attorney, Agent, or Firm* — Nixon Peabody LLP

(57) ABSTRACT

According to some implementations of the present disclosure, a method for determining a remaining useful life of an interface of a respiratory therapy system is disclosed. Acoustic data associated with an acoustic reflection of an acoustic signal is received. The acoustic reflection is indicative of a portion of a structural shape of the interface. The received acoustic data is analyzed to identify a physical feature of the portion of the structural shape of the interface. The physical feature is compared to a reference feature. Based at least in part on the comparison, the remaining useful life of the interface is determined.

16 Claims, 9 Drawing Sheets

(56) References Cited

U.S. PATENT DOCUMENTS 6,675,797 B1 * 1/2004 Berthon-Jones ............................ A61M 16/0875 128/204.23
7,798,143 B1 * 9/2010 Kirby .................. A61M 16/024 128/204.21
8,985,108 B2 * 3/2015 Ahmad ................. A61M 16/00 128/204.23
9,358,353 B2 6/2016 Armitstead et al.
10,492,720 B2 12/2019 Phillips et al.
10,660,563 B2 5/2020 McDarby et al.
11,358,014 B2 * 6/2022 Farmer ................. G01M 3/226
2005/0076906 A1 * 4/2005 Johnson ............ A61M 16/0051 128/204.21
2013/0037028 A1 * 2/2013 Farrugia .............. A61B 5/4818 128/204.23
2013/0047982 A1 * 2/2013 Tobias ................... A62B 9/006 128/205.12
2013/0118500 A1 * 5/2013 Stevens ............... A61M 16/024 128/205.25
2014/0088373 A1 * 3/2014 Phillips .................... A61B 5/05 600/301
2014/0190481 A1 * 7/2014 Jam ..................... A61M 16/024 128/205.24
2014/0190485 A1 * 7/2014 Milne ................. A61M 16/024 128/205.23
2014/0260667 A1 * 9/2014 Berkcan ................ A61M 16/00 73/861.28
2016/0106941 A1 * 4/2016 Hickey ............ A61M 15/0086 128/203.29
2017/0239432 A1 * 8/2017 Delangre .............. A61M 16/06
2017/0361045 A1 * 12/2017 Fu ..................... A61M 16/0066
2018/0243528 A1 * 8/2018 Zapol .................... A61M 16/12
2018/0272081 A1 * 9/2018 Porter ................... A61M 16/12
2018/0353717 A1 * 12/2018 Buschke ........... A61M 16/0003
2019/0358473 A1 * 11/2019 Szasz ..................... A62B 9/006
2020/0001035 A1 * 1/2020 VanPelt ............. A61M 16/0051
2020/0008709 A1 * 1/2020 Martin .............. A61M 16/0666
2020/0254201 A1 * 8/2020 Bender, II ......... A61M 16/0087
2020/0282161 A1 * 9/2020 Chamtie ........... A61M 16/0069
2020/0337634 A1 10/2020 McDarby et al.
2020/0376218 A1 * 12/2020 Mansfield ......... A61M 16/0051
2020/0383580 A1 * 12/2020 Shouldice ............ A61B 5/0205

FOREIGN PATENT DOCUMENTS

WO 2014/047310 A1 3/2014
WO 2016/061629 A1 4/2016
WO 2017/132726 A1 8/2017
WO 2018/050913 A1 3/2018
WO 2019/122413 A1 6/2019
WO 2019/122414 A1 6/2019
WO 2020/104465 A2 5/2020
WO WO-2020220091 A1 * 11/2020 ........ A61M 16/0051
WO WO-2021130681 A1 * 7/2021 ........... A61B 5/4833

* cited by examiner

SYSTEMS AND METHODS FOR DETERMINING A REMAINING USEFUL LIFE OF AN INTERFACE OF A RESPIRATORY THERAPY SYSTEM

CROSS-REFERENCE TO RELATED APPLICATIONS

This application claims the benefit of, and priority to, U.S. Provisional Patent Application No. 63/334,528 filed on Apr. 25, 2022, which is hereby incorporated by reference herein in its entirety.

TECHNICAL FIELD

The present disclosure relates generally to systems and methods for analyzing an interface of a respiratory therapy system, and more particularly, to systems and methods for determining a remaining useful life of an interface of a respiratory therapy system.

BACKGROUND

Many individuals suffer from sleep-related and/or respiratory-related disorders such as, for example, Periodic Limb Movement Disorder (PLMD), Restless Leg Syndrome (RLS), Sleep-Disordered Breathing (SDB) such as Obstructive Sleep Apnea (OSA) and Central Sleep Apnea (CSA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders. These disorders are often treated using respiratory therapy systems.

Each respiratory system generally has a respiratory therapy device connected to a user interface (e.g., a mask) via a conduit and optionally a connector. The user wears the user interface and is supplied a flow of pressurized air from the respiratory therapy device via the conduit. The user interface generally is a specific category and type of user interface for the user, such as direct or indirect connections for the category of user interface, and full face mask, a partial face mask, nasal mask, or nasal pillows for the type of user interface. In addition to the specific category and type, the user interface generally is a specific model made by a specific manufacturer.

Different user interfaces may wear out at different rates. When a user interface is worn, it can negatively impact therapy. Some users may even discontinue use of the respiratory therapy system because of the discomfort and/or inaccurate therapy caused by the worn user interface. Thus, it is advantageous to know the remaining useful life of the user interface of a respiratory therapy system for providing optimal therapy to the user. The present disclosure is directed to solving these and other problems.

SUMMARY

According to some implementations of the present disclosure, a method for determining a remaining useful life of an interface of a respiratory therapy system is disclosed. Acoustic data associated with an acoustic reflection of an acoustic signal is received. The acoustic reflection is indicative of a portion of a structural shape of the interface. The received acoustic data is analyzed to identify a physical feature of the portion of the structural shape of the interface. The physical feature is compared to a reference feature. Based at least in part on the comparison, the remaining useful life of the interface is determined.

According to some implementations of the present disclosure, a system includes a control system and a memory. The control system includes one or more processors. The memory has stored thereon machine readable instructions. The control system is coupled to the memory, and any one of the methods disclosed herein is implemented when the machine executable instructions in the memory are executed by at least one of the one or more processors of the control system.

According to some implementations of the present disclosure, a system for characterizing a user interface and/or a vent of a respiratory therapy system includes a control system configured to implement any one of the methods disclosed herein.

According to some implementations of the present disclosure, a computer program product includes instructions which, when executed by a computer, cause the computer to carry out any one of the methods disclosed herein.

The above summary is not intended to represent each implementation or every aspect of the present disclosure. Additional features and benefits of the present disclosure are apparent from the detailed description and figures set forth below.

Figure 1:
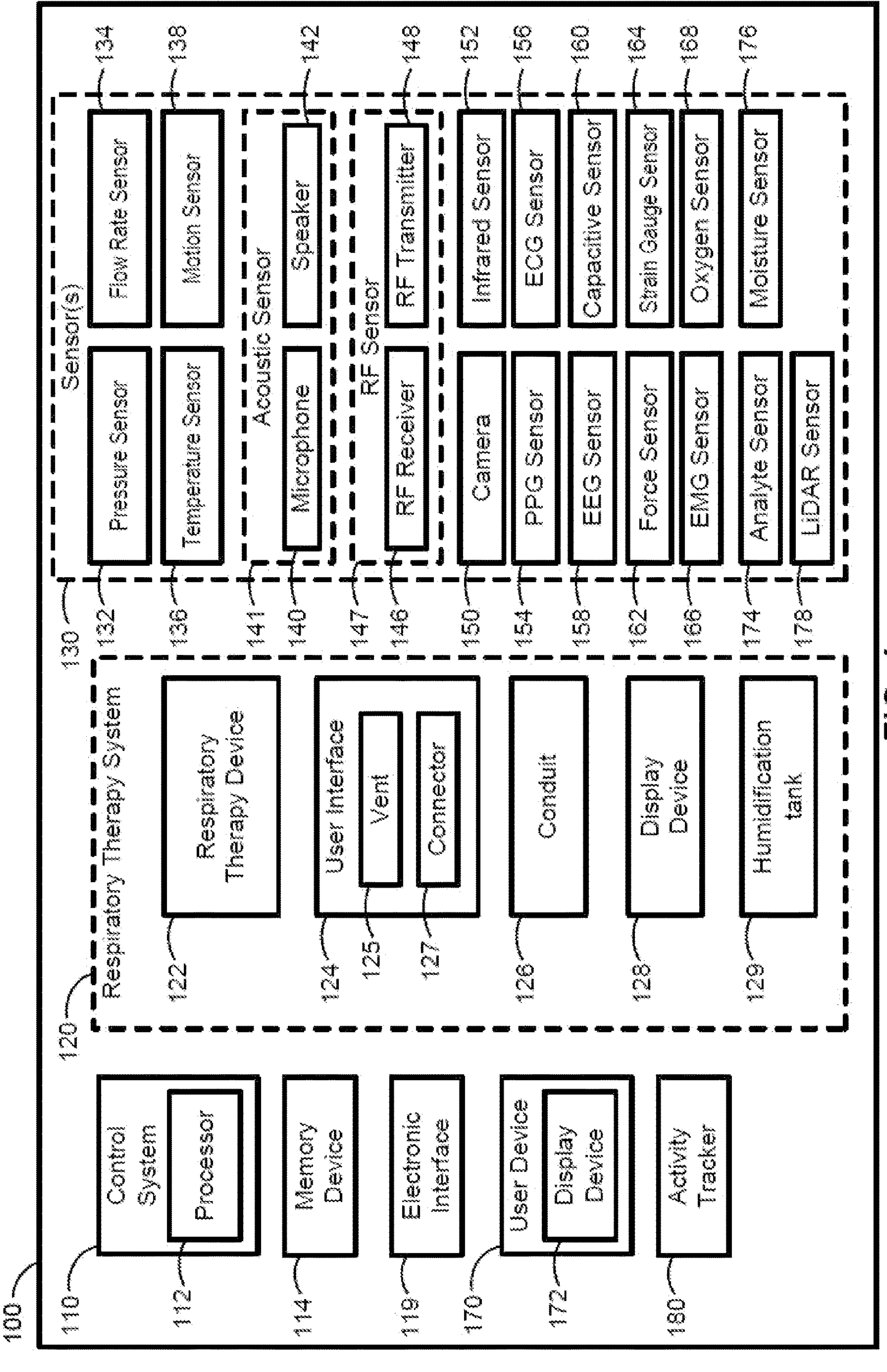
FIG. 1 is a functional block diagram of a system, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

The present disclosure is described with reference to the attached figures, where like reference numerals are used throughout the figures to designate similar or equivalent elements. The figures are not drawn to scale, and are provided merely to illustrate the instant disclosure. Several aspects of the disclosure are described below with reference to example applications for illustration.

Many individuals suffer from sleep-related and/or respiratory disorders. Examples of sleep-related and/or respiratory disorders include Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas (e.g., mixed apneas and hypopneas), Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall. More generally, an apnea generally refers to the cessation of breathing caused by blockage of the air (Obstructive Sleep Apnea) or the stopping of the breathing function (often referred to as Central Sleep Apnea). Typically, the individual will stop breathing for between about 15 seconds and about 30 seconds during an obstructive sleep apnea event.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increase depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for 10 seconds or longer leading to arousal from sleep and which does not fulfill the criteria for an apnea or hypopnea event. In 1999, the AASM Task Force defined RERAs as "a sequence of breaths characterized by increasing respiratory effort leading to an arousal from sleep, but which does not meet criteria for an apnea or hypopnea. These events must fulfil both of the following criteria: 1. pattern of progressively more negative esophageal pressure, terminated by a sudden change in pressure to a less negative level and an arousal; 2. the event lasts 10 seconds or longer. In 2000, the study "Non-Invasive Detection of Respiratory Effort-Related Arousals (RERAs) by a Nasal Cannula/Pressure Transducer System" done at NYU School of Medicine and published in Sleep, vol. 23, No. 6, pp. 763-771, demonstrated that a Nasal Cannula/Pressure Transducer System was adequate and reliable in the detection of RERAs. A RERA detector may be based on a real flow signal derived from a respiratory therapy (e.g., PAP) device. For example, a flow limitation measure may be determined based on a flow signal. A measure of arousal may then be derived as a function of the flow limitation measure and a measure of sudden increase in ventilation. One such method is described in WO 2008/138040 and U.S. Pat. No. 9,358,353, assigned to ResMed Ltd., each of which is hereby incorporated by reference herein in its entirety.

Cheyne-Stokes Respiration (CSR) is another form of sleep disordered breathing. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

Individuals with diabetes who also use a respiratory therapy system (for example to treat SDB) can experience positive and/or negative interactions. For example, the use of the respiratory therapy system can impact the efficacy of the individual's diabetes treatment plan (which could include a diabetes medication plan, a diet plan, an exercise plan, etc.). The impact on the efficacy of the individual's diabetes treatment plan can be positive or negative, and thus it can be difficult for these individuals to use a respiratory therapy system in adherence with a respiratory therapy plan, while also adhering to a diabetes treatment plan that remains effective. Thus, it is advantageous to monitor these individuals, and to make various adjustments to their diabetes treatment plans and their use of respiratory therapy systems in order to mitigate, optimize, etc. any interactions between their diabetes treatment plan and their respiratory therapy plan The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Referring to FIG. 1, a system 100, according to some implementations of the present disclosure, is illustrated. The system 100 includes a control system 110, a memory device 114, an electronic interface 119, one or more sensors 130, and one or more user devices 170. In some implementations, the system 100 further optionally includes a respiratory therapy system 120, and an activity tracker 180.

The control system 110 includes one or more processors 112 (hereinafter, processor 112). The control system 110 is generally used to control (e.g., actuate) the various components of the system 100 and/or analyze data obtained and/or generated by the components of the system 100. The processor 112 can be a general or special purpose processor or microprocessor. While one processor 112 is illustrated in FIG. 1, the control system 110 can include any number of processors (e.g., one processor, two processors, five processors, ten processors, etc.) that can be in a single housing, or located remotely from each other. The control system 110 (or any other control system) or a portion of the control system 110 such as the processor 112 (or any other processor(s) or portion(s) of any other control system), can be used to carry out one or more steps of any of the methods described and/or claimed herein. The control system 110 can be coupled to and/or positioned within, for example, a housing of the user device 170, a portion (e.g., a housing) of the respiratory therapy system 120, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1, the system 100 can include any suitable number of memory devices 114 (e.g., one memory device, two memory devices, five memory devices, ten memory devices, etc.). The memory device 114 can be coupled to and/or positioned within a housing of a respiratory therapy device 122 of the respiratory therapy system 120, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 stores a user profile associated with the user. The user profile can include, for example, demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a geographic location of the user, a relationship status, a family history of insomnia or sleep apnea, an employment status of the user, an educational status of the user, a socioeconomic status of the user, or any combination thereof. The medical information can include, for example, information indicative of one or more medical conditions associated with the user, medication usage by the user, or both. The medical information data can further include a multiple sleep latency test (MSLT) result or score and/or a Pittsburgh Sleep Quality Index (PSQI) score or value. The self-reported user feedback can include information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or acoustic data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using an RF communication protocol, a Wi-Fi communication protocol, a Bluetooth communication protocol, over a cellular network, etc.). The electronic interface 119 can include an antenna, a receiver (e.g., an RF receiver), a transmitter (e.g., an RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory therapy system 120. The respiratory therapy system 120 can include a respiratory pressure therapy (RPT) device 122 (referred to herein as respiratory therapy device 122), a user interface 124, a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory therapy device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory therapy system 120 is generally used to treat individuals suffering from one or more sleep-related respiratory disorders (e.g., obstructive sleep apnea, central sleep apnea, or mixed sleep apnea).

The respiratory therapy device 122 is generally used to generate pressurized air that is delivered to a user (e.g., using one or more motors that drive one or more compressors). In some implementations, the respiratory therapy device 122 generates continuous constant air pressure that is delivered to the user. In other implementations, the respiratory therapy device 122 generates two or more predetermined pressures (e.g., a first predetermined air pressure and a second predetermined air pressure). In still other implementations, the respiratory therapy device 122 is configured to generate a variety of different air pressures within a predetermined range. For example, the respiratory therapy device 122 can deliver at least about 6 $cmH_2O$, at least about 10 $cmH_2O$, at least about 20 $cmH_2O$, between about 6 $cmH_2O$ and about 10 $cmH_2O$, between about 7 $cmH_2O$ and about 12 $cmH_2O$, etc. The respiratory therapy device 122 can also deliver pressurized air at a predetermined flow rate between, for example, about −20 L/min and about 150 L/min, while maintaining a positive pressure (relative to the ambient pressure).

The user interface 124 engages a portion of the user's face and delivers pressurized air from the respiratory therapy device 122 to the user's airway to aid in preventing the airway from narrowing and/or collapsing during sleep. This may also increase the user's oxygen intake during sleep. Generally, the user interface 124 engages the user's face such that the pressurized air is delivered to the user's airway via the user's mouth, the user's nose, or both the user's mouth and nose. Together, the respiratory therapy device 122, the user interface 124, and the conduit 126 form an air pathway fluidly coupled with an airway of the user. The pressurized air also increases the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 $cmH_2O$ relative to ambient pressure. For other forms of therapy, such as the delivery of oxygen, the user interface may not include a seal sufficient to facilitate delivery to the airways of a supply of gas at a positive pressure of about 10 $cmH_2O$. In some implementations, the user interface 124 may include a connector 127 and one or more vents 125, which are described in more detail with reference to FIGS. 3A-3B, 4A-4B, and 5A-5B. In some implementations, the connector 127 is distinct from, but couplable to, the user interface 124 (and/or conduit 126).

Figure 2:
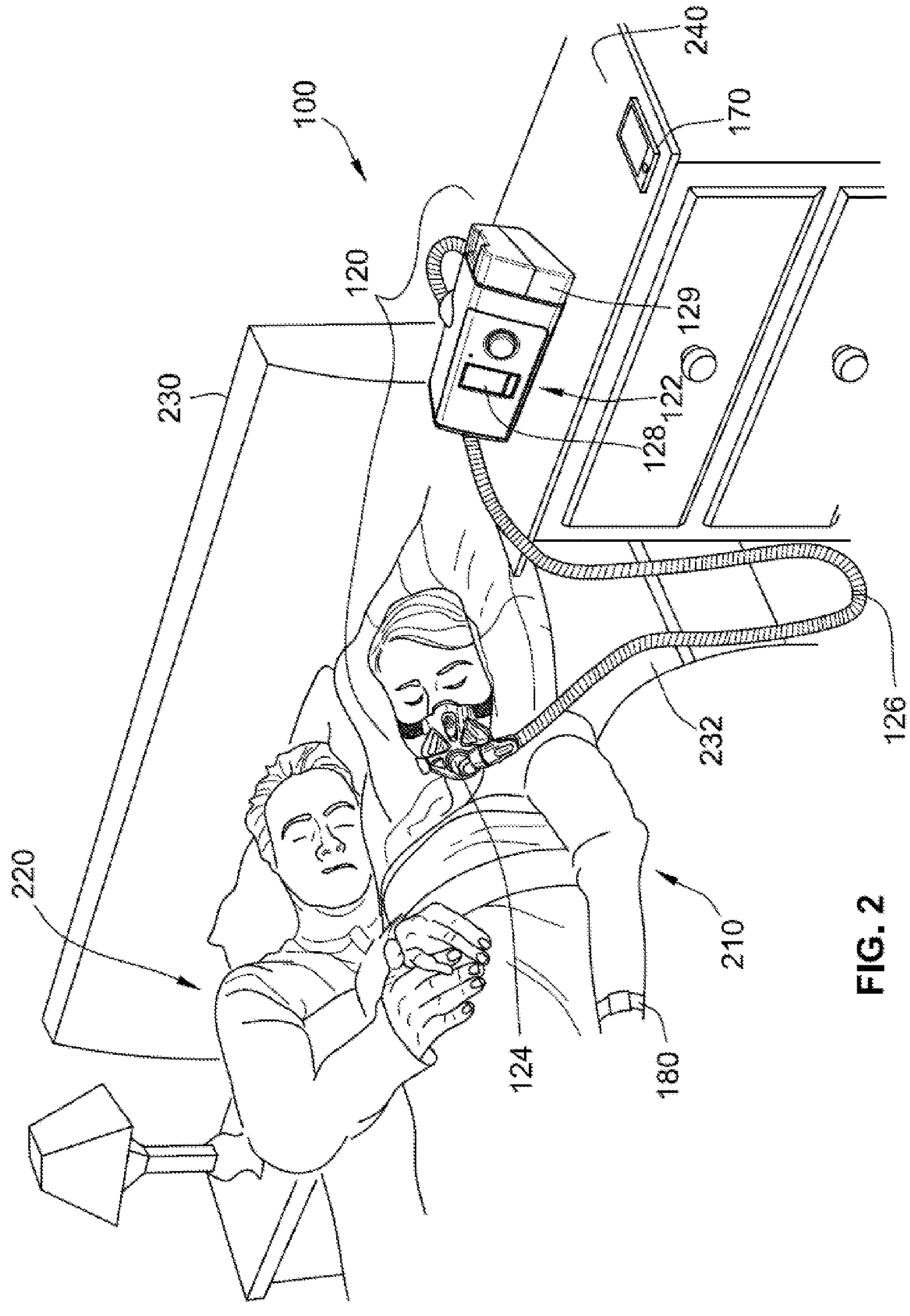
FIG. 2 is a perspective view of at least a portion of the system of FIG. 1, a user, and a bed partner, according to some implementations of the present disclosure.

As shown in FIG. 2, in some implementations, the user interface 124 is a facial mask (e.g., a full face mask) that covers the nose and mouth of the user. Alternatively, the user interface 124 can be a nasal mask that provides air to the nose of the user or a nasal pillow mask that delivers air directly to the nostrils of the user. The user interface 124 can include a plurality of straps forming, for example, a headgear for aiding in positioning and/or stabilizing the interface on a portion of the user (e.g., the face) and a conformal cushion (e.g., silicone, plastic, foam, etc.) that aids in providing an air-tight seal between the user interface 124 and the user. The user interface 124 can also include one or more vents for permitting the escape of carbon dioxide and other gases exhaled by the user 210. In other implementations, the user interface 124 includes a mouthpiece (e.g., a night guard mouthpiece molded to conform to the teeth of the user, a mandibular repositioning device, etc.).

Figure 3A:
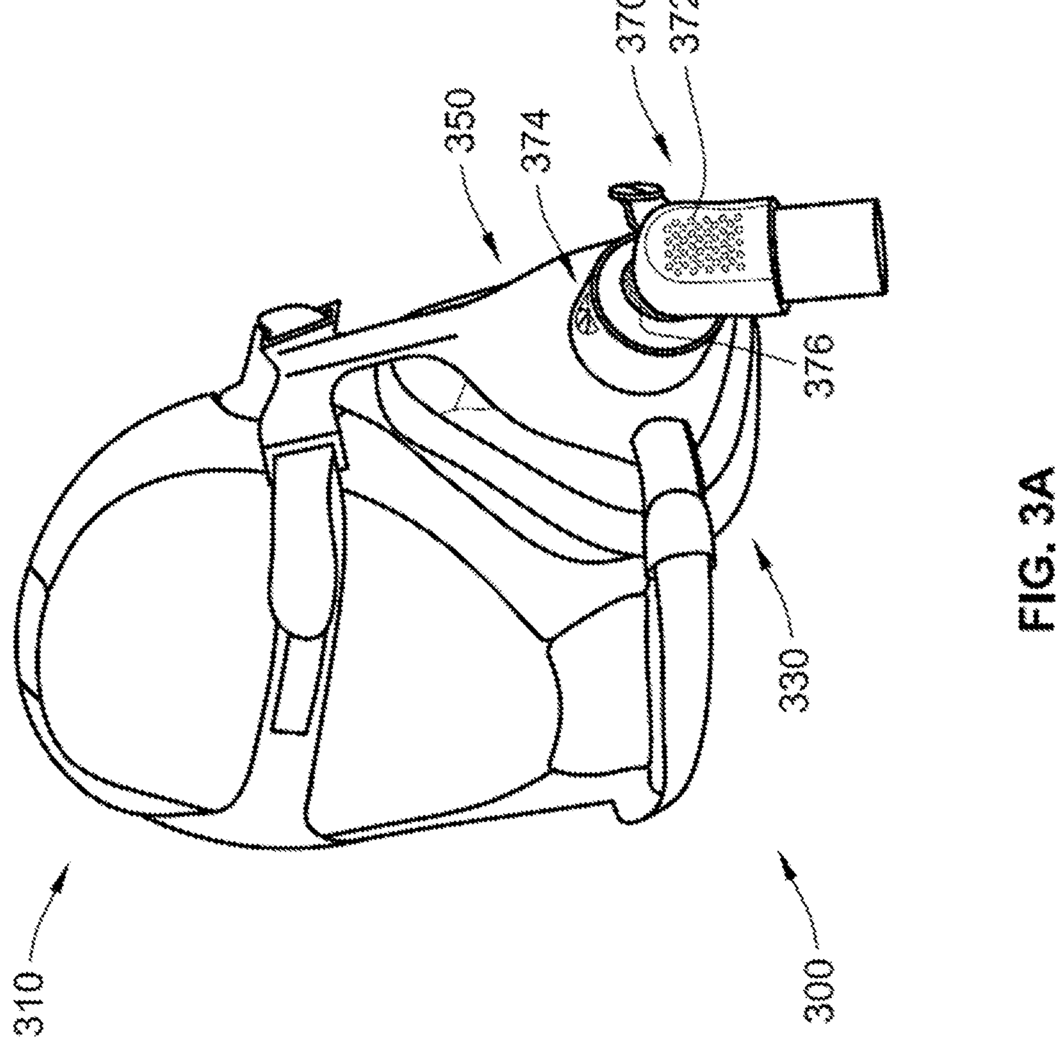
FIG. 3A is a perspective view of one category of user interfaces, according to some implementations of the present disclosure.
Figure 3B:
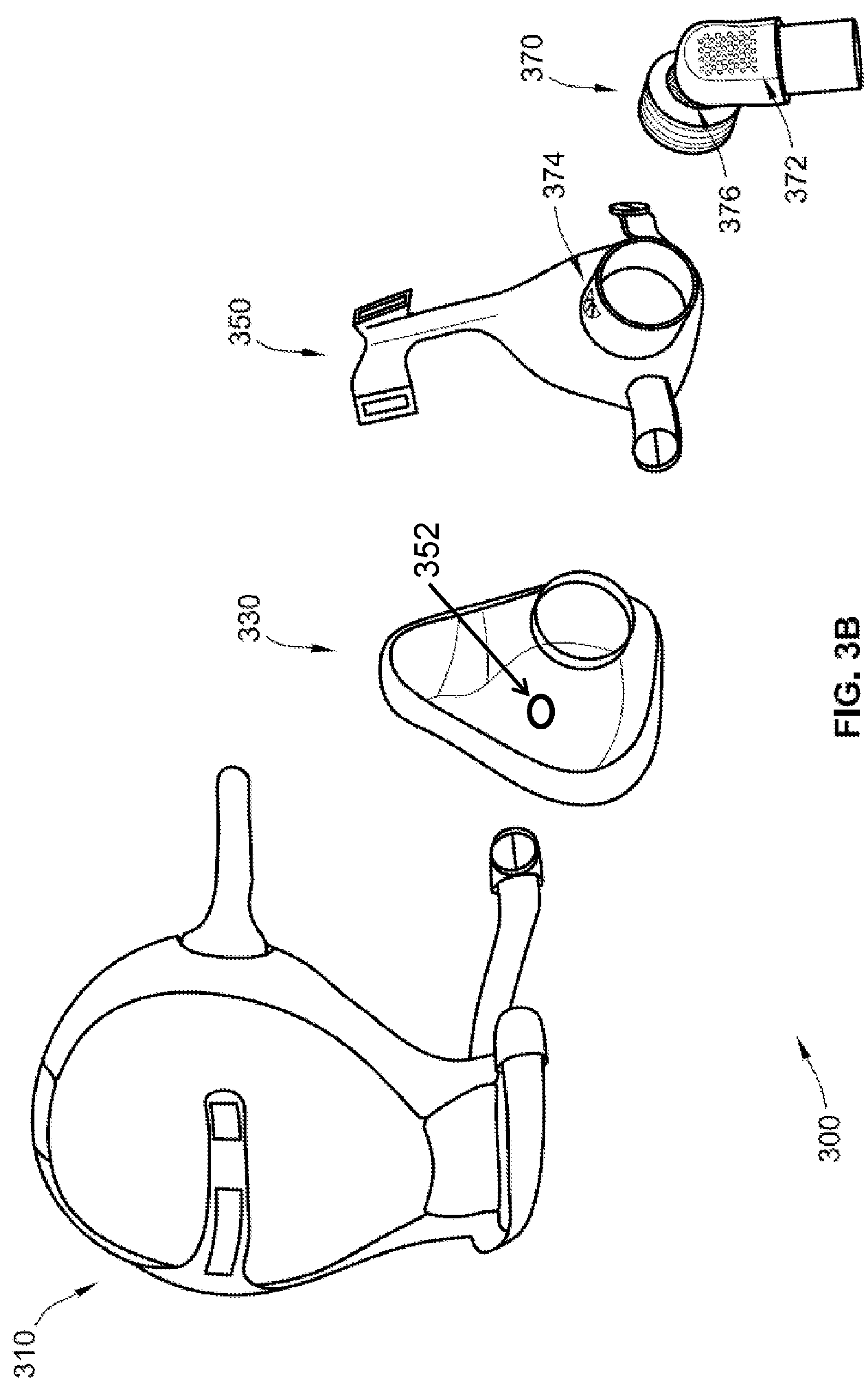
FIG. 3B is an exploded view of the user interface of FIG. 3A, according to some implementations of the present disclosure.

FIGS. 3A and 3B illustrate a perspective view and an exploded view, respectively, of one implementation of a directly connected user interface ("direct category" user interfaces), according to aspects of the present disclosure. The direct category of a user interface 300 generally includes a cushion 330 and a frame 350 that define a volume of space around the mouth and/or nose of the user. When in use, the volume of space receives pressurized air for passage into the user's airways. In some embodiments, the cushion 330 and frame 350 of the user interface 300 form a unitary component of the user interface. The user interface 300 assembly may further be considered to comprise a headgear 310, which in the case of the user interface 300 is generally a strap assembly, and optionally a connector 370. The headgear 310 is configured to be positioned generally about at least a portion of a user's head when the user wears the user interface 300. The headgear 310 can be coupled to the frame 350 and positioned on the user's head such that the user's head is positioned between the headgear 310 and the frame 350. The cushion 330 is positioned between the user's face and the frame 350 to form a seal on the user's face. The optional connector 370 is configured to couple to the frame 350 and/or cushion 330 at one end and to a conduit of a respiratory therapy device (not shown). The pressurized air can flow directly from the conduit of the respiratory therapy system into the volume of space defined by the cushion 330 (or cushion 330 and frame 350) of the user interface 300 through the connector 370). From the user interface 300, the pressurized air reaches the user's airway through the user's mouth, nose, or both. Alternatively, where the user interface 300 does not include the connector 370, the conduit of the respiratory therapy system can connect directly to the cushion 330 and/or the frame 350.

In some implementations, the connector 370 may include a plurality of vents 372 located on the main body of the connector 370 itself and/or a plurality of vents 376 ("diffuser vents") in proximity to the frame 350, for permitting the escape of carbon dioxide ($CO_2$) and other gases exhaled by the user when the respiratory therapy device is active. In some implementations, the frame 350 may include at least one anti-asphyxia valve (AAV) 374, which allows $CO_2$ and other gases exhaled by the user to escape in the event that the vents (e.g., the vents 372 or 376) fail when the respiratory therapy device is active. In general, AAVs (e.g., the AAV 374) are always present for full face masks (as a safety feature), however, the diffuser vents and vents placed on mask or connector (usually an array of orifices in the mask material itself or a mesh made of some sort of fabric, in many cases replaceable) are not both present (e.g., some masks might have only the diffuser vents such as the plurality of vents 376, other masks might have only the plurality of vents 372 on the connector itself).

For indirectly connected user interfaces ("indirect category" user interfaces), and as will be described in greater detail below, the conduit of the respiratory therapy system connects indirectly with the cushion and/or frame of the user interface. Another element of the user interface—besides any connector—is between the conduit of the respiratory therapy system and the cushion and/or frame. This additional element delivers the pressurized air to the volume of space formed between the cushion (or frame, or cushion and frame) of the user interface and the user's face, from the conduit of the respiratory therapy system. Thus, pressurized air is delivered indirectly from the conduit of the respiratory therapy system into the volume of space defined by the cushion (or the cushion and frame) of the user interface against the user's face. Moreover, according to some implementations, the indirectly connected category of user interfaces can be described as being at least two different categories: "indirect headgear" and "indirect conduit". For the indirect headgear category, the conduit of the respiratory therapy system connects to a headgear conduit, optionally via a connector, which in turn connects to the cushion (or frame, or cushion and frame). The headgear is therefore configured to deliver the pressurized air from the conduit of the respiratory therapy system to the cushion (or frame, or cushion and frame) of the user interface. This headgear conduit within the headgear of the user interface is therefore configured to deliver the pressurized air from the conduit of the respiratory therapy system to the cushion of the user interface.

In some implementations, the user interface 300 may further include a physical feature 352 (FIG. 3B). For example, in some implementations, the physical feature 352 includes a hole in the user interface, and the hole progressively expands over time based on usage. Additionally or alternatively, in some implementations, the physical feature 352 includes a fin on the user interface, and the fin progressively dissolves over time based on usage. While it is shown that the physical feature 352 is located on the cushion 330, it is contemplated that the physical feature 352 can be anywhere on the user interface 300, such as on the frame 350 or the connector 370. Similar physical features may be included in other types of user interfaces, such as the user interface 400 and the user interface 500 described below.

Figure 4A:
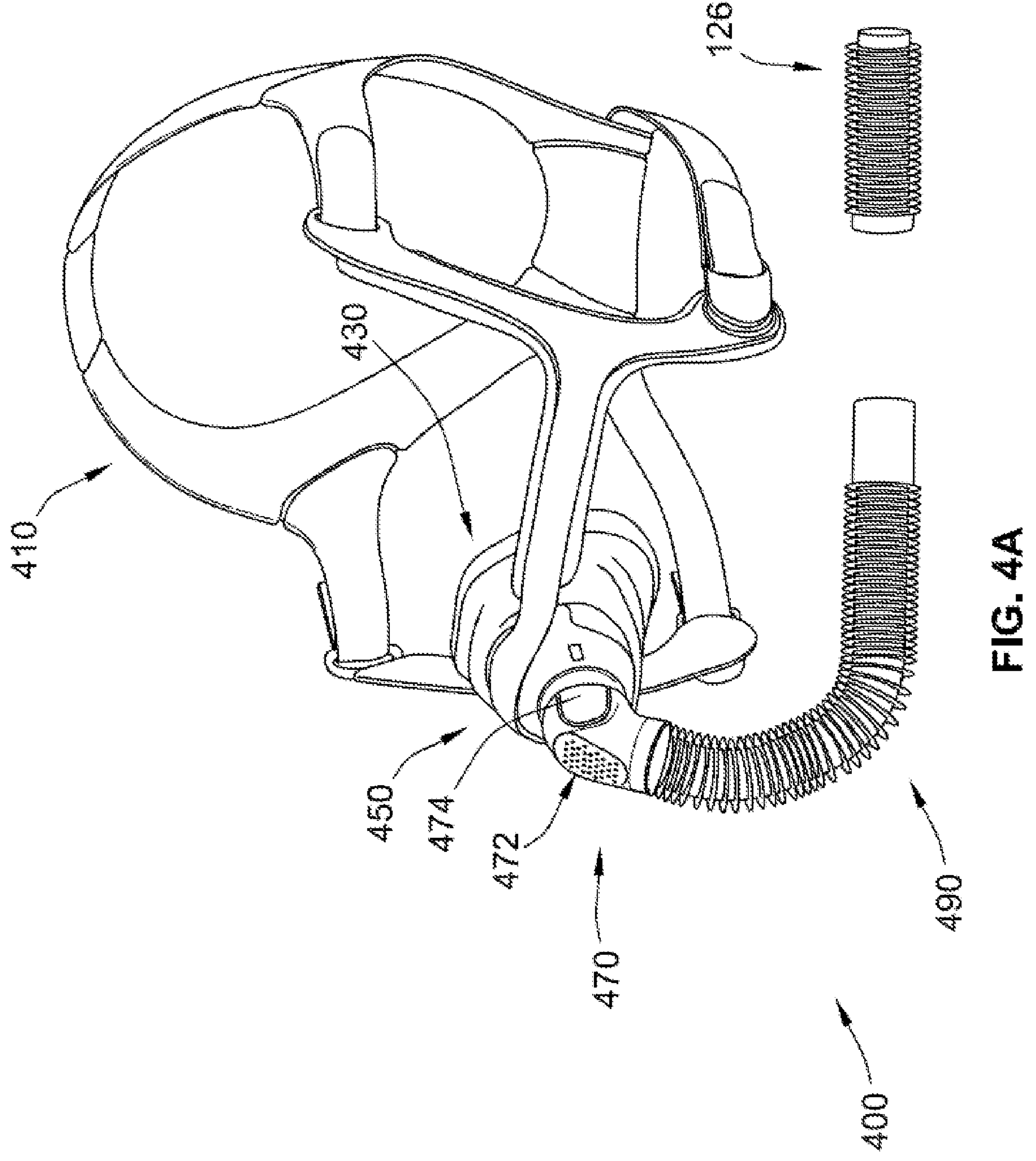
FIG. 4A is a perspective view of another category of user interfaces, according to some implementations of the present disclosure.
Figure 4B:
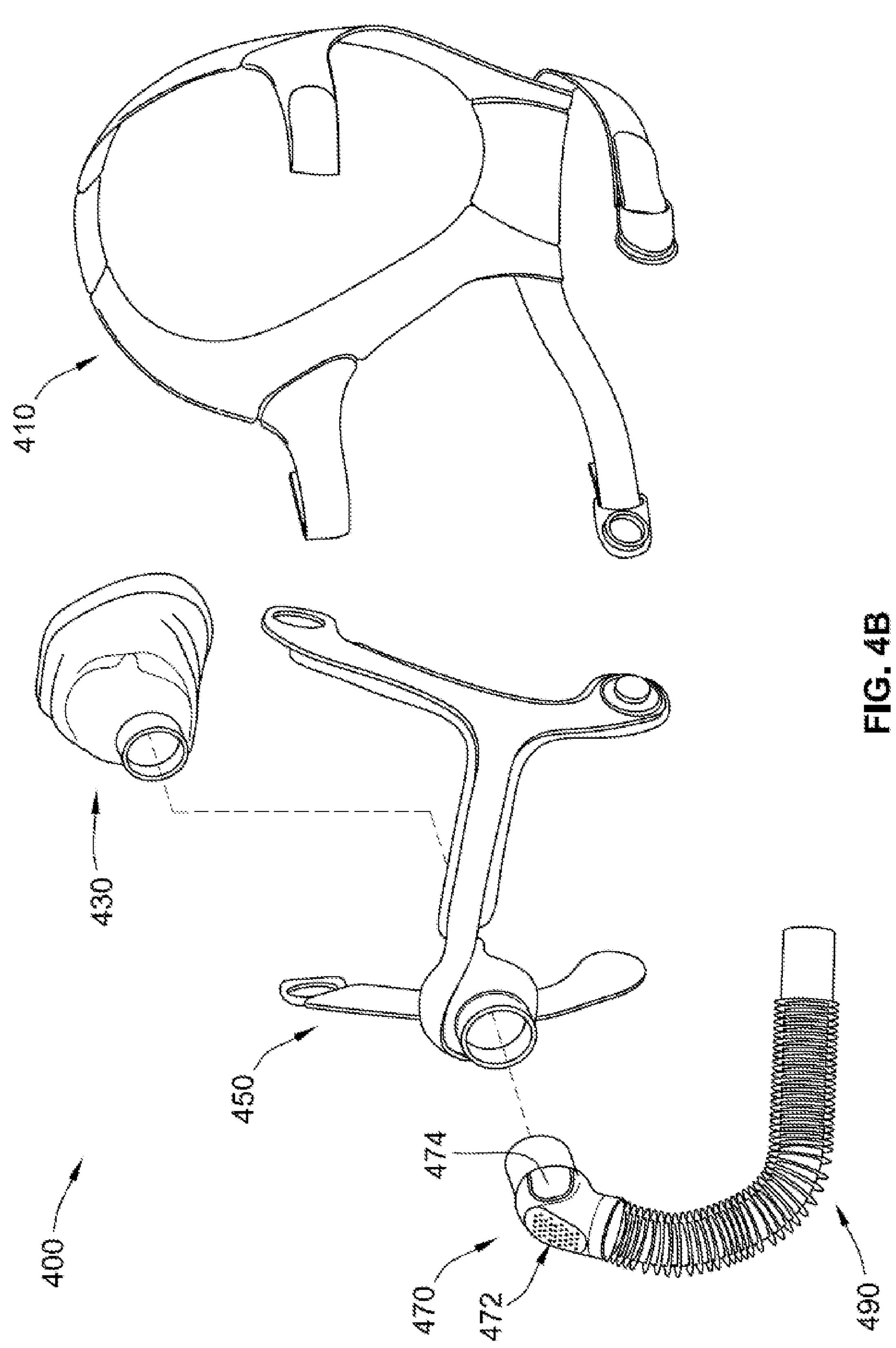
FIG. 4B is an exploded view of the user interface of FIG. 4A, according to some implementations of the present disclosure.

FIGS. 4A and 4B illustrate a perspective view and an exploded view, respectively, of one implementation of an indirect conduit user interface 400, according to aspects of the present disclosure. The indirect conduit user interface 400 includes a cushion 430 and a frame 450. In some embodiments, the cushion 430 and frame 450 form a unitary component of the user interface 400. The indirect conduit user interface 400 may further be considered to include a headgear 410, such as a strap assembly, a connector 470, and a user interface conduit 490 (often referred to in the art as a "minitube" or a "flexitube").

Generally, the user interface conduit 490 is (i) more flexible than the conduit 126 of the respiratory therapy system, (ii) has a diameter smaller than the diameter of the conduit 126 of the respiratory therapy system, or both (i) and (ii). Similar to the headgear 310 of user interface 300, the headgear 410 of user interface 400 is configured to be positioned generally about at least a portion of a user's head when the user wears the user interface 400. The headgear 410 can be coupled to the frame 450 and positioned on the user's head such that the user's head is positioned between the headgear 410 and the frame 450. The cushion 430 is positioned between the user's face and the frame 450 to form a seal on the user's face. The connector 470 is configured to couple to the frame 450 and/or cushion 430 at one end and to the conduit 490 of the user interface 400 at the other end. In other implementations, the conduit 490 may connect directly to frame 450 and/or cushion 430. The conduit 490, at the opposite end relative to the frame 450 and cushion 430, is configured to connect to the conduit 126 (FIG. 4A) of the respiratory therapy system (not shown). The pressurized air can flow from the conduit 126 (FIG. 4A) of the respiratory therapy system, through the user interface conduit 490, and the connector 470, and into a volume of space define by the cushion 430 (or cushion 430 and frame 450) of the user interface 400 against a user's face. From the volume of space, the pressurized air reaches the user's airway through the user's mouth, nose, or both.

In view of the above configuration, the user interface 400 is an indirectly connected user interface because pressurized air is delivered from the conduit 126 (FIG. 4A) of the respiratory therapy system (not shown) to the cushion 430 (or frame 450, or cushion 430 and frame 450) through the user interface conduit 490, rather than directly from the conduit 126 (FIG. 4A) of the respiratory therapy system.

As shown, in some implementations, the connector 470 includes a plurality of vents 472 for permitting the escape of carbon dioxide ($CO_2$) and other gases exhaled by the user when the respiratory therapy device is active. In some such implementations, each of the plurality of vents 472 is an opening that may be angled relative to the thickness of the connector wall through which the opening is formed. The angled openings can reduce noise of the $CO_2$ and other gases escaping to the atmosphere. Because of the reduced noise, acoustic signal associated with the plurality of vents 472 may be more apparent to an internal microphone, as opposed to an external microphone.

In some implementations, the connector 470 optionally includes at least one valve 474 for permitting the escape of $CO_2$ and other gases exhaled by the user when the respiratory therapy device is inactive. In some implementations, the valve 474 (an example of an anti-asphyxia valve) includes a silicone flap that is a failsafe component, which allows $CO_2$ and other gases exhaled by the user to escape in the event that the vents 472 fail when the respiratory therapy device is active. In some such implementations, when the silicone flap is open, the valve opening is much greater than each vent opening, and therefore less likely to be blocked by occlusion materials.

Figure 5A:
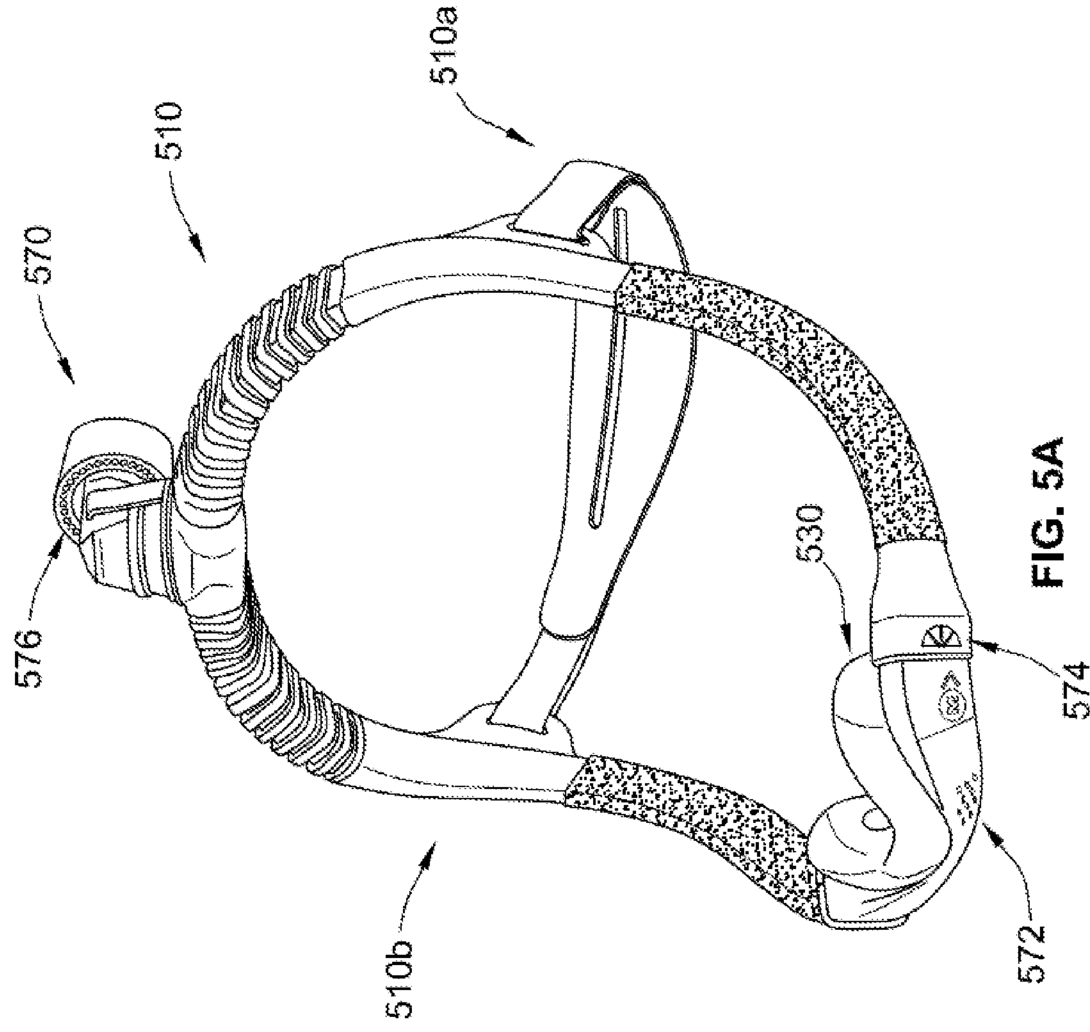
FIG. 5A is a perspective view of another category of user interfaces, according to some implementations of the present disclosure.
Figure 5B:
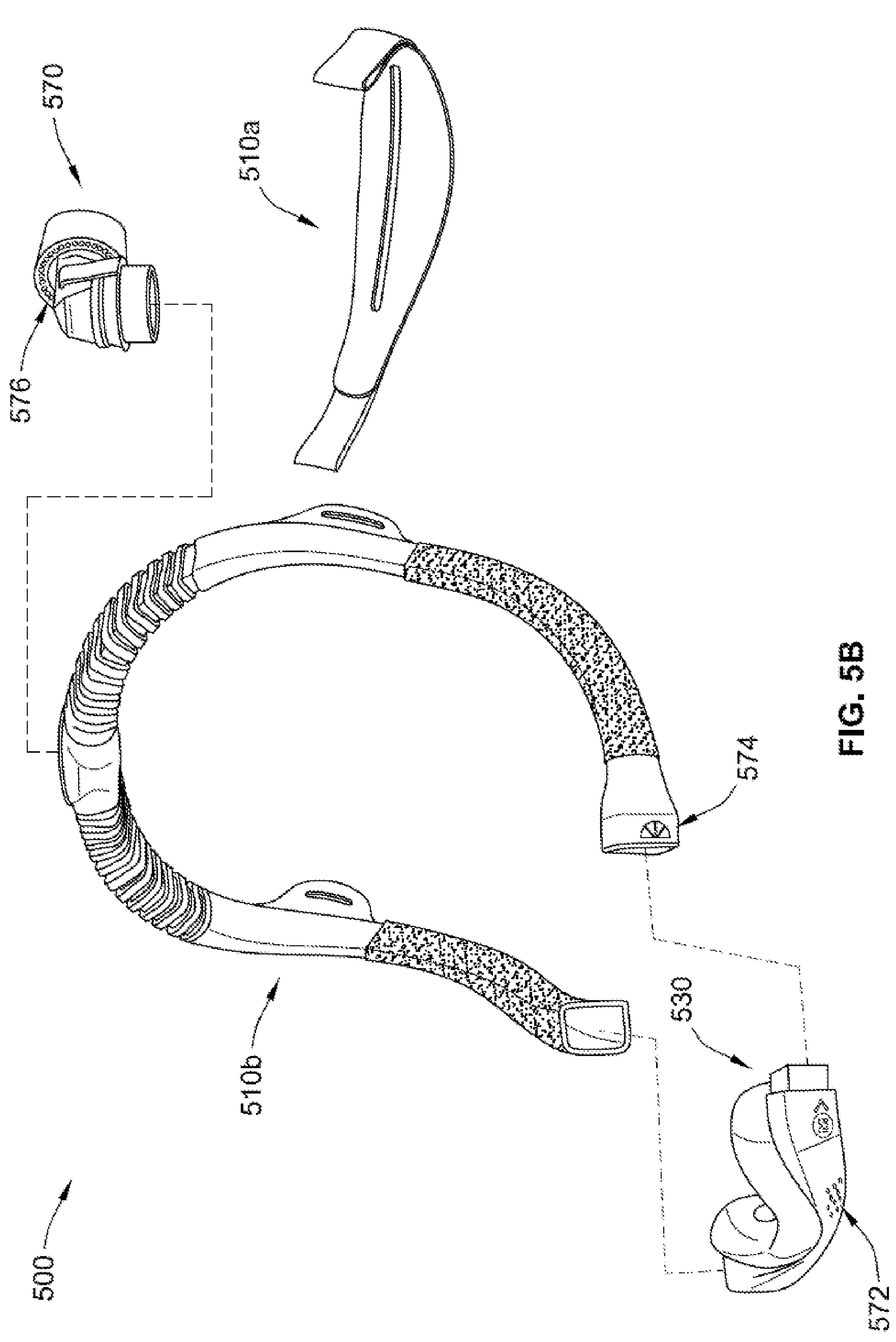
FIG. 5B is an exploded view of the user interface of FIG. 5A, according to some implementations of the present disclosure.

FIGS. 5A and 5B illustrate a perspective view and an exploded view, respectively, of one implementation of an indirect headgear user interface 500, according to aspects of the present disclosure. The indirect headgear user interface 500 includes a cushion 530. The indirect headgear user interface 500 may further be considered to comprise headgear 510 (which can comprise strap 510*a* and a headgear conduit 510*b*, and a connector 570. Similar to the user interfaces 300 and 400, the headgear 510 is configured to be positioned generally about at least a portion of a user's head when the user wears the user interface 500. The headgear 510 includes a strap 510*a* that can be coupled to the headgear conduit 510*b* and positioned on the user's head such that the user's head is positioned between the strap 510*a* and the headgear conduit 510*b*. The cushion 530 is positioned between the user's face and the headgear conduit 510*b* to form a seal on the user's face. The connector 570 is configured to couple to the headgear 510 at one end and a conduit of the respiratory therapy system at the other end. In other implementations, the connector 570 can be optional and the headgear 510 can alternatively connect directly to conduit of the respiratory therapy system. The headgear conduit 510*b* may be configured to deliver pressurized air from the conduit of the respiratory therapy system to the cushion 530, or more specifically, to the volume of space around the mouth and/or nose of the user and enclosed by the user cushion. Thus, the headgear conduit 510*b* is hollow to provide a passageway for the pressurized air. Both sides of the headgear conduit 510*b* can be hollow to provide two passageways for the pressurized air. Alternatively, only one side of the headgear conduit 510*b* can be hollow to provide a single passageway. In the implementation illustrated in FIGS. 5A and 5B, headgear conduit 510*b* comprises two passageways which, in use, are positioned at either side of a user's head/face. Alternatively, only one passageway of the headgear conduit 510*b* can be hollow to provide a single passageway. The pressurized air can flow from the conduit of the respiratory therapy system, through the connector 570 and the headgear conduit 510*b*, and into the volume of space between the cushion 530 and the user's face. From the volume of space between the cushion 530 and the user's face, the pressurized air reaches the user's airway through the user's mouth, nose, or both.

In some implementations, the cushion 530 may include a plurality of vents 572 on the cushion 530 itself. Additionally or alternatively, in some implementations, the connector 570 may include a plurality of vents 576 ("diffuser vents") in proximity to the headgear 510, for permitting the escape of carbon dioxide ($CO_2$) and other gases exhaled by the user when the respiratory therapy device is active. In some implementations, the headgear 510 may include at least one anti-asphyxia valve (AAV) 574 in proximity to the cushion 530, which allows $CO_2$ and other gases exhaled by the user to escape in the event that the vents (e.g., the vents 572 or 576) fail when the respiratory therapy device is active.

In view of the above configuration, the user interface 500 is an indirect headgear user interface because pressurized air is delivered from the conduit of the respiratory therapy system to the volume of space between the cushion 530 and the user's face through the headgear conduit 510*b*, rather than directly from the conduit of the respiratory therapy system to the volume of space between the cushion 530 and the user's face.

In one or more implementations, the distinction between the direct category and the indirect category can be defined in terms of a distance the pressurized air travels after leaving the conduit of the respiratory therapy device and before reaching the volume of space defined by the cushion of the user interface forming a seal with the user's face, exclusive of a connector of the user interface that connects to the conduit. This distance is shorter, such as less than 1 centimeter (cm), less than 2 cm, less than 3 cm, less than 4 cm, or less than 5 cm, for direct category user interfaces than for indirect category user interfaces. This is because the pressurized air travels through the additional element of, for example, the user interface conduit 490 or the headgear conduit 510*b* between the conduit of the respiratory therapy system before reaching the volume of space defined by the cushion (or cushion and frame) of the user interface forming a seal with the user's face for indirect category user interfaces.

Referring back to FIG. 1, the conduit 126 (also referred to as an air circuit or tube) allows the flow of air between two components of a respiratory therapy system 120, such as the respiratory therapy device 122 and the user interface 124. In some implementations, there can be separate limbs of the conduit for inhalation and exhalation. In other implementations, a single limb conduit is used for both inhalation and exhalation.

One or more of the respiratory therapy device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory therapy device 122.

Figure 6:
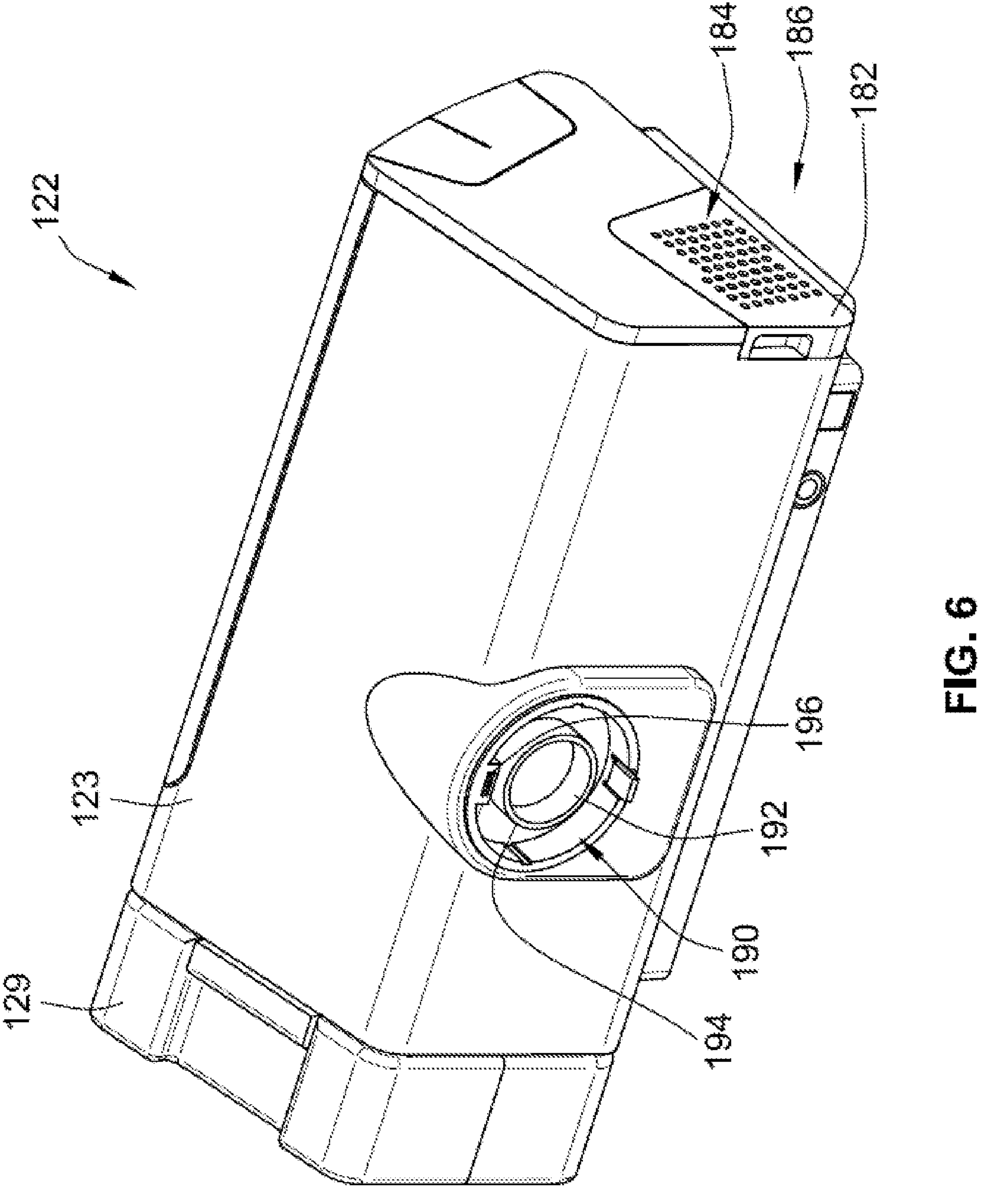
FIG. 6 is a rear perspective view of a respiratory therapy device of the system of FIG. 1, according to some implementations of the present disclosure.

Referring briefly to FIG. 6, a perspective view of the back side of the respiratory therapy device 122 that includes a housing 123, an air inlet 186, and an air outlet 190. The air inlet 186 includes an inlet cover 182 movable between a closed position and an open position. The air inlet cover 182 includes one or more air inlet apertures 184 defined therein. The respiratory therapy device 122 includes a blower motor configured to draw air in through the one or more air inlet apertures 184 defined in the air inlet cover 182. The motor is further configured to cause pressurized air to flow through the humidification tank 129 and out of the air outlet 190. The conduit 126 can be fluidly coupled to the air outlet 190, such that the air flows from the air outlet 190 and into the conduit 126. The air outlet 190 is partially formed by an internal conduit 192 extending through the housing 123 from the interior of the respiratory therapy device 122. A seal 194 is positioned around the end of the internal conduit 192 to ensure that substantially all of the air that exits through the air outlet 190 flows into the conduit 126.

Referring back to FIG. 1, the display device 128 is generally used to display image(s) including still images, video images, or both and/or information regarding the respiratory therapy device 122. For example, the display device 128 (and/or the display device 172 of the user device 170) can provide information regarding the status of the respiratory therapy device 122 (e.g., whether the respiratory therapy device 122 is on/off, the pressure of the air being delivered by the respiratory therapy device 122, the temperature of the air being delivered by the respiratory therapy device 122, etc.) and/or other information (e.g., a sleep score and/or a therapy score, also referred to as a myAir™ score, such as described in WO 2016/061629, which is hereby incorporated by reference herein in its entirety; the current date/time; personal information for the user 210; etc.). In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory therapy device 122.

The humidification tank 129 is coupled to or integrated in the respiratory therapy device 122 and includes a reservoir of water that can be used to humidify the pressurized air delivered from the respiratory therapy device 122. The respiratory therapy device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. The humidification tank 129 can be fluidly coupled to a water vapor inlet of the air pathway and deliver water vapor into the air pathway via the water vapor inlet, or can be formed in-line with the air pathway as part of the air pathway itself. In other implementations, the respiratory therapy device 122 or the conduit 126 can include a waterless humidifier. The waterless humidifier can incorporate sensors that interface with other sensor positioned elsewhere in system 100.

The respiratory therapy system 120 can be used, for example, as a ventilator or as a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure.

Referring to FIG. 2, a portion of the system 100 (FIG. 1), according to some implementations, is illustrated. A user 210 of the respiratory therapy system 120 and a bed partner 220 are located in a bed 230 and are laying on a mattress 232. The user interface 124 (also referred to herein as a mask, e.g., a full facial mask) can be worn by the user 210 during a sleep session. The user interface 124 is fluidly coupled and/or connected to the respiratory therapy device 122 via the conduit 126. In turn, the respiratory therapy device 122 delivers pressurized air to the user 210 via the conduit 126 and the user interface 124 to increase the air pressure in the throat of the user 210 to aid in preventing the airway from closing and/or narrowing during sleep. The respiratory therapy device 122 can include the display device 128, which can allow the user to interact with the respiratory therapy device 122. The respiratory therapy device 122 can also include the humidification tank 129, which stores the water used to humidify the pressurized air. The respiratory therapy device 122 can be positioned on a nightstand 240 that is directly adjacent to the bed 230 as shown in FIG. 2, or more generally, on any surface or structure that is generally adjacent to the bed 230 and/or the user 210. The user can also wear the activity tracker 180 while lying on the mattress 232 in the bed 230.

Referring to back to FIG. 1, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or more sensors 130 are configured to output sensor data that is received and stored in the memory device 114 or one or more other memory devices. The sensors 130 can also include, an electrooculography (EOG) sensor, a peripheral oxygen saturation ($SpO_2$) sensor, a galvanic skin response (GSR) sensor, a carbon dioxide ($CO_2$) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the infrared sensor 152, the photoplethysmogram (PPG) sensor 154, the electrocardiogram (ECG) sensor 156, the electroencephalography (EEG) sensor 158, the capacitive sensor 160, the force sensor 162, the strain gauge sensor 164, the electromyography (EMG) sensor 166, the oxygen sensor 168, the analyte sensor 174, the moisture sensor 176, and the LiDAR sensor 178, more generally, the one or more sensors 130 can include any combination and any number of each of the sensors described and/or shown herein.

As described herein, the system 100 generally can be used to generate physiological data associated with a user (e.g., a user of the respiratory therapy system 120 shown in FIG. 2) during a sleep session. The physiological data can be analyzed to generate one or more sleep-related parameters, which can include any parameter, measurement, etc. related to the user during the sleep session. The one or more sleep-related parameters that can be determined for the user 210 during the sleep session include, for example, an Apnea-Hypopnea Index (AHI) score, a sleep score, a flow signal, a respiration signal, a respiration rate, an inspiration amplitude, an expiration amplitude, an inspiration-expiration ratio, a number of events per hour, a pattern of events, a stage, pressure settings of the respiratory therapy device 122, a heart rate, a heart rate variability, movement of the user 210, temperature, EEG activity, EMG activity, arousal, snoring, choking, coughing, whistling, wheezing, or any combination thereof.

The one or more sensors 130 can be used to generate, for example, physiological data, acoustic data, or both. Physiological data generated by one or more of the sensors 130 can be used by the control system 110 to determine a sleep-wake signal associated with the user 210 (FIG. 2) during the sleep session and one or more sleep-related parameters. The sleep-wake signal can be indicative of one or more sleep states, including wakefulness, relaxed wakefulness, micro-awakenings, or distinct sleep stages such as, for example, a rapid eye movement (REM) stage, a first non-REM stage (often referred to as "N1"), a second non-REM stage (often referred to as "N2"), a third non-REM stage (often referred to as "N3"), or any combination thereof. Methods for determining sleep states and/or sleep stages from physiological data generated by one or more sensors, such as the one or more sensors 130, are described in, for example, WO 2014/047310, US 2014/0088373, WO 2017/132726, WO 2019/122413, U.S. Pat. Nos. 10,492,720, 10,660,563, US 2020/0337634, US 2020/0383580, and WO 2019/122414, each of which is hereby incorporated by reference herein in its entirety.

In some implementations, the sleep-wake signal described herein can be timestamped to indicate a time that the user enters the bed, a time that the user exits the bed, a time that the user attempts to fall asleep, etc. The sleep-wake signal can be measured by the one or more sensors 130 during the sleep session at a predetermined sampling rate, such as, for example, one sample per second, one sample per 30 seconds, one sample per minute, etc. In some implementations, the sleep-wake signal can also be indicative of a respiration signal, a respiration rate, an inspiration amplitude, an expiration amplitude, an inspiration-expiration ratio, a number of events per hour, a pattern of events, pressure settings of the respiratory therapy device 122, or any combination thereof during the sleep session. The event(s) can include snoring, apneas, central apneas, obstructive apneas, mixed apneas, hypopneas, a mask leak (e.g., from the user interface 124), a restless leg, a sleeping disorder, choking, an increased heart rate, labored breathing, an asthma attack, an epileptic episode, a seizure, or any combination thereof. The one or more sleep-related parameters that can be determined for the user during the sleep session based on the sleep-wake signal include, for example, a total time in bed, a total sleep time, a sleep onset latency, a wake-after-sleep-onset parameter, a sleep efficiency, a fragmentation index, or any combination thereof. As described in further detail herein, the physiological data and/or the sleep-related parameters can be analyzed to determine one or more sleep-related scores.

Physiological data and/or acoustic data generated by the one or more sensors 130 can also be used to determine a respiration signal associated with a user during a sleep session. The respiration signal is generally indicative of respiration or breathing of the user during the sleep session. The respiration signal can be indicative of and/or analyzed to determine (e.g., using the control system 110) one or more sleep-related parameters, such as, for example, a respiration rate, a respiration rate variability, an inspiration amplitude, an expiration amplitude, an inspiration-expiration ratio, an occurrence of one or more events, a number of events per hour, a pattern of events, a sleep state, a sleet stage, an apnea-hypopnea index (AHI), pressure settings of the respiratory therapy device 122, or any combination thereof. The one or more events can include snoring, apneas, central apneas, obstructive apneas, mixed apneas, hypopneas, a mask leak (e.g., from the user interface 124), a cough, a restless leg, a sleeping disorder, choking, an increased heart rate, labored breathing, an asthma attack, an epileptic episode, a seizure, increased blood pressure, a fever, a sneeze, a gasp, the presence of an illness such as the common cold or the flu, an elevated stress level, or any combination thereof. Events can be detected by any means known in the art such as described in, for example, U.S. Pat. Nos. 5,245,995, 6,502,572, WO 2018/050913, WO 2020/104465, each of which is incorporated by reference herein in its entirety. Many of the described sleep-related parameters are physiological parameters, although some of the sleep-related parameters can be considered to be non-physiological parameters. Other types of physiological and/or non-physiological parameters can also be determined, either from the data from the one or more sensors 130, or from other types of data.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory therapy system 120 and/or ambient pressure. In such implementations, the pressure sensor 132 can be coupled to or integrated in the respiratory therapy device 122. The pressure sensor 132 can be, for example, a capacitive sensor, an electromagnetic sensor, a piezoelectric sensor, a strain-gauge sensor, an optical sensor, an inductive sensor, a resistive sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. Examples of flow rate sensors (such as, for example, the flow rate sensor 134) are described in WO 2012/012835, which is hereby incorporated by reference herein in its entirety. In some implementations, the flow rate sensor 134 is used to determine an air flow rate from the respiratory therapy device 122, an air flow rate through the conduit 126, an air flow rate through the user interface 124, or any combination thereof. In such implementations, the flow rate sensor 134 can be coupled to or integrated in the respiratory therapy device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof. In some implementations, the flow rate sensor 134 is configured to measure a vent flow (e.g., intentional "leak"), an unintentional leak (e.g., mouth leak and/or mask leak), a patient flow (e.g., air into and/or out of lungs), or any combination thereof. In some implementations, the flow rate data can be analyzed to determine cardiogenic oscillations of the user. In one example, the pressure sensor 132 can be used to determine a blood pressure of a user.

The temperature sensor 136 outputs temperature data that can be stored in the memory device 114 and/or analyzed by the processor 112 of the control system 110. In some implementations, the temperature sensor 136 generates temperatures data indicative of a core body temperature of the user 210 (FIG. 2), a skin temperature of the user 210, a temperature of the air flowing from the respiratory therapy device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user 210 during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user and proximal to the user interface 124, and configured to detect features of the pulse shape, speed, amplitude, or volume. In some implementations, the motion sensor 138 alternatively or additionally generates one or more signals representing bodily movement of the user, from which may be obtained a signal representing a sleep state of the user; for example, via a respiratory movement of the user. In some implementations, the motion data from the motion sensor 138 can be used in conjunction with additional data from another sensor 130 to determine the sleep state of the user.

The microphone 140 can be located at any location relative to the respiratory therapy system 120 and in acoustic communication with the airflow in the respiratory therapy system 120. For example, the respiratory therapy system 120 may include a microphone 140 (*i*) coupled externally to the conduit 126, (ii) positioned within, optionally at least partially within the respiratory therapy device 122, (iii) coupled externally to the user interface 124, (iv) coupled directly or indirectly to a headgear associated with the user interface 124, or in any other suitable location. In some implementations, the microphone 140 is coupled to a mobile device (for example, the user device 170 or a smart speaker(s) such as Google Home, Amazon Echo, Alexa etc.) that is communicatively coupled to the respiratory therapy system 120.

In some implementations, the microphone 140 is positioned on or at least partially outside of a housing of the respiratory therapy device 122. For example, the microphone 140 may be at least partially movable relative to the housing of the respiratory therapy device 122 to aid in being directed to the user 210 (FIG. 2). For example, the microphone 340 can be rotated between about 5° and about 355° towards the user 210.

In some implementations, the microphone 140 is configured to be in direct fluid communication with the airflow in the respiratory therapy system 120. For example, the microphone 140 may be (i) positioned at least partially within the conduit 126, (ii) positioned at least partially within the respiratory therapy device 122, optionally positioned at least partially within a component of the respiratory therapy device 122, which is in fluid communication with the conduit 126, or (iii) positioned at least partially within the user interface 124, the user interface 124 being in fluid communication with the conduit 126. Further, in some implementations, the microphone 140 is electrically connected with a circuit board (for example, connected physically, such as mounted on, the circuit board directly or indirectly) of the respiratory therapy device 122, which may be in acoustic communication (for example, via a small duct and/or a silicone window as in a stethoscope) or in fluid communication with the airflow in the respiratory therapy system 120.

The microphone 140 outputs sound and/or acoustic data that can be stored in the memory device 114 and/or analyzed by the processor 112 of the control system 110. The acoustic data generated by the microphone 140 is reproducible as one or more sound(s) during a sleep session (e.g., sounds from the user 210). The acoustic data form the microphone 140 can also be used to identify (e.g., using the control system 110) an event experienced by the user during the sleep session, as described in further detail herein. The microphone 140 can be coupled to or integrated in the respiratory therapy device 122, the user interface 124, the conduit 126, or the user device 170. In some implementations, the system 100 includes a plurality of microphones (e.g., two or more microphones and/or an array of microphones with beamforming) such that sound data generated by each of the plurality of microphones can be used to discriminate the sound data generated by another of the plurality of microphones.

The microphone 140 can be coupled to or integrated in the respiratory therapy system 120 (or the system 100) generally in any configuration. For example, the microphone 140 can be disposed inside the respiratory therapy device 122, the user interface 124, the conduit 126, or other components. The microphone 140 can also be positioned adjacent to or coupled to the outside of the respiratory therapy device 122, the outside of the user interface 124, the outside of the conduit 126, or outside of any other components. The microphone 140 could also be a component of the user device 170 (e.g., the microphone 140 is a microphone of a smart phone). The microphone 140 can be integrated into the user interface 124, the conduit 126, the respiratory therapy device 122, or any combination thereof. In general, the microphone 140 can be located at any point within or adjacent to the air pathway of the respiratory therapy system 120, which includes at least the motor of the respiratory therapy device 122, the user interface 124, and the conduit 126. Thus, the air pathway can also be referred to as the acoustic pathway.

The speaker 142 outputs sound waves that are audible to a user of the system 100 (e.g., the user 210 of FIG. 2). The speaker 142 can be used, for example, as an alarm clock or to play an alert or message to the user 210 (e.g., in response to an event). In some implementations, the speaker 142 can be used to communicate the acoustic data generated by the microphone 140 to the user. The speaker 142 can be coupled to or integrated in the respiratory therapy device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which is hereby incorporated by reference herein in its entirety. In such implementations, the speaker 142 generates or emits sound waves at a predetermined interval and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user 210 or the bed partner 220 (FIG. 2). Based at least in part on the data from the microphone 140 and/or the speaker 142, the control system 110 can determine a location of the user 210 (FIG. 2) and/or one or more of the sleep-related parameters described in herein such as, for example, a respiration signal, a respiration rate, an inspiration amplitude, an expiration amplitude, an inspiration-expiration ratio, a number of events per hour, a pattern of events, a sleep state, a sleep stage, pressure settings of the respiratory therapy device 122, or any combination thereof. In such a context, a SONAR sensor may be understood to concern an active acoustic sensing, such as by generating and/or transmitting ultrasound and/or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above, each of which is hereby incorporated by reference herein in its entirety.

In some implementations, the sensors 130 include (i) a first microphone that is the same as, or similar to, the microphone 140, and is integrated in the acoustic sensor 141 and (ii) a second microphone that is the same as, or similar to, the microphone 140, but is separate and distinct from the first microphone that is integrated in the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. An RF receiver (either the RF receiver 146 and the RF transmitter 148 or another RF pair) can also be used for wireless communication between the control system 110, the respiratory therapy device 122, the one or more sensors 130, the user device 170, or any combination thereof. While the RF receiver 146 and RF transmitter 148 are shown as being separate and distinct elements in FIG. 1, in some implementations, the RF receiver 146 and RF transmitter 148 are combined as a part of an RF sensor 147 (e.g. a RADAR sensor). In some such implementations, the RF sensor 147 includes a control circuit. The specific format of the RF communication can be Wi-Fi, Bluetooth, or the like.

In some implementations, the RF sensor 147 is a part of a mesh system. One example of a mesh system is a Wi-Fi mesh system, which can include mesh nodes, mesh router(s), and mesh gateway(s), each of which can be mobile/movable or fixed. In such implementations, the Wi-Fi mesh system includes a Wi-Fi router and/or a Wi-Fi controller and one or more satellites (e.g., access points), each of which include an RF sensor that the is the same as, or similar to, the RF sensor 147. The Wi-Fi router and satellites continuously communicate with one another using Wi-Fi signals. The Wi-Fi mesh system can be used to generate motion data based on changes in the Wi-Fi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or any combination thereof) that can be stored in the memory device 114. The image data from the camera 150 can be used by the control system 110 to determine one or more of the sleep-related parameters described herein, such as, for example, one or more events (e.g., periodic limb movement or restless leg syndrome), a respiration signal, a respiration rate, an inspiration amplitude, an expiration amplitude, an inspiration-expiration ratio, a number of events per hour, a pattern of events, a sleep state, a sleep stage, or any combination thereof. Further, the image data from the camera 150 can be used to, for example, identify a location of the user, to determine chest movement of the user 210 (FIG. 2), to determine air flow of the mouth and/or nose of the user 210, to determine a time when the user 210 enters the bed 230 (FIG. 2), and to determine a time when the user 210 exits the bed 230. In some implementations, the camera 150 includes a wide angle lens or a fish eye lens. The camera 150 can also be used to track eye movements, pupil dilation (if one or both of the user's eyes are open), blink rate, or any changes during REM sleep. The camera 150 can also be used to track the position of the user, which can impact the duration and/or severity of apneic episodes in users with positional obstructive sleep apnea.

The infrared (IR) sensor 152 outputs infrared image data reproducible as one or more infrared images (e.g., still images, video images, or both) that can be stored in the memory device 114. The infrared data from the IR sensor 152 can be used to determine one or more sleep-related parameters during a sleep session, including a temperature of the user 210 and/or movement of the user 210. The IR sensor 152 can also be used in conjunction with the camera 150 when measuring the presence, location, and/or movement of the user 210. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user 210 (FIG. 2) that can be used to determine one or more sleep-related parameters, such as, for example, a heart rate, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user 210, embedded in clothing and/or fabric that is worn by the user 210, embedded in and/or coupled to the user interface 124 and/or its associated headgear (e.g., straps, etc.), etc.

The ECG sensor 156 outputs physiological data associated with electrical activity of the heart of the user 210. In some implementations, the ECG sensor 156 includes one or more electrodes that are positioned on or around a portion of the user 210 during the sleep session. The physiological data from the ECG sensor 156 can be used, for example, to determine one or more of the sleep-related parameters described herein.

The EEG sensor 158 outputs physiological data associated with electrical activity of the brain of the user 210. In some implementations, the EEG sensor 158 includes one or more electrodes that are positioned on or around the scalp of the user 210 during the sleep session. The physiological data from the EEG sensor 158 can be used, for example, to determine a sleep state and/or a sleep stage of the user 210 at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, a pulse oximeter (e.g., $SpO_2$ sensor), or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user 210. The data output by the analyte sensor 174 can be stored in the memory device 114 and used by the control system 110 to determine the identity and concentration of any analytes in the breath of the user 210. In some implementations, the analyte sensor 174 is positioned near a mouth of the user 210 to detect analytes in breath exhaled from the user 210's mouth. For example, when the user interface 124 is a facial mask that covers the nose and mouth of the user 210, the analyte sensor 174 can be positioned within the facial mask to monitor the user 210's mouth breathing. In other implementations, such as when the user interface 124 is a nasal mask or a nasal pillow mask, the analyte sensor 174 can be positioned near the nose of the user 210 to detect analytes in breath exhaled through the user's nose. In still other implementations, the analyte sensor 174 can be positioned near the user 210's mouth when the user interface 124 is a nasal mask or a nasal pillow mask. In this implementation, the analyte sensor 174 can be used to detect whether any air is inadvertently leaking from the user 210's mouth. In some implementations, the analyte sensor 174 is a volatile organic compound (VOC) sensor that can be used to detect carbon-based chemicals or compounds. In some implementations, the analyte sensor 174 can also be used to detect whether the user 210 is breathing through their nose or mouth. For example, if the data output by an analyte sensor 174 positioned near the mouth of the user 210 or within the facial mask (in implementations where the user interface 124 is a facial mask) detects the presence of an analyte, the control system 110 can use this data as an indication that the user 210 is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory therapy device 122, etc.). Thus, in some implementations, the moisture sensor 176 can be coupled to or integrated in the user interface 124 or in the conduit 126 to monitor the humidity of the pressurized air from the respiratory therapy device 122. In other implementations, the moisture sensor 176 is placed near any area where moisture levels need to be monitored. The moisture sensor 176 can also be used to monitor the humidity of the ambient environment surrounding the user 210, for example, the air inside the bedroom. The moisture sensor 176 can also be used to track the user's biometric response to environmental changes.

The Light Detection and Ranging (LiDAR) sensor 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

In some implementations, the one or more sensors 130 also include a galvanic skin response (GSR) sensor, a blood flow sensor, a respiration sensor, a pulse sensor, a sphygmomanometer sensor, an oximetry sensor, a SONAR sensor, a RADAR sensor, a blood glucose sensor, a color sensor, a pH sensor, an air quality sensor, a tilt sensor, a rain sensor, a soil moisture sensor, a water flow sensor, an alcohol sensor, or any combination thereof.

While shown separately in FIG. 1, any combination of the one or more sensors 130 can be integrated in and/or coupled to any one or more of the components of the system 100, including the respiratory therapy device 122, the user interface 124, the conduit 126, the humidification tank 129, the control system 110, the user device 170, the activity tracker 180, or any combination thereof. For example, the microphone 140 and the speaker 142 can be integrated in and/or coupled to the user device 170 and the pressure sensor 132 and/or flow rate sensor 134 are integrated in and/or coupled to the respiratory therapy device 122. In some implementations, at least one of the one or more sensors 130 is not coupled to the respiratory therapy device 122, the control system 110, or the user device 170, and is positioned generally adjacent to the user 210 during the sleep session (e.g., positioned on or in contact with a portion of the user 210, worn by the user 210, coupled to or positioned on the nightstand, coupled to the mattress, coupled to the ceiling, etc.).

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, a sleep state, an apnea-hypopnea index (AHI), or any combination thereof. The one or more events can include snoring, apneas, central apneas, obstructive apneas, mixed apneas, hypopneas, a mask leak, a cough, a restless leg, a sleeping disorder, choking, an increased heart rate, labored breathing, an asthma attack, an epileptic episode, a seizure, increased blood pressure, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 (FIG. 1) includes a display device 172. The user device 170 can be, for example, a mobile device such as a smart phone, a tablet, a gaming console, a smart watch, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices can be used by and/or included in the system 100.

In some implementations, the system 100 also includes an activity tracker 180. The activity tracker 180 is generally used to aid in generating physiological data associated with the user. The activity tracker 180 can include one or more of the sensors 130 described herein, such as, for example, the motion sensor 138 (e.g., one or more accelerometers and/or gyroscopes), the PPG sensor 154, and/or the ECG sensor 156. The physiological data from the activity tracker 180 can be used to determine, for example, a number of steps, a distance traveled, a number of steps climbed, a duration of physical activity, a type of physical activity, an intensity of physical activity, time spent standing, a respiration rate, an average respiration rate, a resting respiration rate, a maximum he respiration art rate, a respiration rate variability, a heart rate, an average heart rate, a resting heart rate, a maximum heart rate, a heart rate variability, a number of calories burned, blood oxygen saturation, electrodermal activity (also known as skin conductance or galvanic skin response), or any combination thereof. In some implementations, the activity tracker 180 is coupled (e.g., electronically or physically) to the user device 170.

In some implementations, the activity tracker 180 is a wearable device that can be worn by the user, such as a smartwatch, a wristband, a ring, or a patch. For example, referring to FIG. 2, the activity tracker 180 is worn on a wrist of the user 210. The activity tracker 180 can also be coupled to or integrated a garment or clothing that is worn by the user. Alternatively still, the activity tracker 180 can also be coupled to or integrated in (e.g., within the same housing) the user device 170. More generally, the activity tracker 180 can be communicatively coupled with, or physically integrated in (e.g., within a housing), the control system 110, the memory device 114, the respiratory therapy system 120, and/or the user device 170.

While the control system 110 and the memory device 114 are described and shown in FIG. 1 as being a separate and distinct component of the system 100, in some implementations, the control system 110 and/or the memory device 114 are integrated in the user device 170 and/or the respiratory therapy device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system according to implementations of the present disclosure. For example, a first alternative system includes the control system 110, the memory device 114, and at least one of the one or more sensors 130 and does not include the respiratory therapy system 120. As another example, a second alternative system includes the control system 110, the memory device 114, at least one of the one or more sensors 130, and the user device 170. As yet another example, a third alternative system includes the control system 110, the memory device 114, the respiratory therapy system 120, at least one of the one or more sensors 130, and the user device 170. Thus, various systems can be formed using any portion or portions of the components shown and described herein and/or in combination with one or more other components.

Referring again to FIG. 2, in some implementations, the control system 110, the memory device 114, any of the one or more sensors 130, or a combination thereof can be located on and/or in any surface and/or structure that is generally adjacent to the bed 230 and/or the user 210. For example, in some implementations, at least one of the one or more sensors 130 can be located at a first position on and/or in one or more components of the respiratory therapy system 120 adjacent to the bed 230 and/or the user 210. The one or more sensors 130 can be coupled to the respiratory therapy system 120, the user interface 124, the conduit 126, the display device 128, the humidification tank 129, or a combination thereof.

Alternatively, or additionally, at least one of the one or more sensors 130 can be located at a second position on and/or in the bed 230 (e.g., the one or more sensors 130 are coupled to and/or integrated in the bed 230). Further, alternatively or additionally, at least one of the one or more sensors 130 can be located at a third position on and/or in the mattress 232 that is adjacent to the bed 230 and/or the user 210 (e.g., the one or more sensors 130 are coupled to and/or integrated in the mattress 232). Alternatively, or additionally, at least one of the one or more sensors 130 can be located at a fourth position on and/or in a pillow that is generally adjacent to the bed 230 and/or the user 210.

Alternatively, or additionally, at least one of the one or more sensors 130 can be located at a fifth position on and/or in the nightstand 240 that is generally adjacent to the bed 230 and/or the user 210. Alternatively, or additionally, at least one of the one or more sensors 130 can be located at a sixth position such that the at least one of the one or more sensors 130 are coupled to and/or positioned on the user 210 (e.g., the one or more sensors 130 are embedded in or coupled to fabric, clothing, and/or a smart device worn by the user 210). More generally, at least one of the one or more sensors 130 can be positioned at any suitable location relative to the user 210 such that the one or more sensors 130 can generate sensor data associated with the user 210.

In some implementations, a primary sensor, such as the microphone 140, is configured to generate acoustic data associated with the user 210 during a sleep session. The acoustic data can be based on, for example, acoustic signals in the conduit 126 of the respiratory therapy system 120. For example, one or more microphones (the same as, or similar to, the microphone 140 of FIG. 1) can be integrated in and/or coupled to (i) a circuit board of the respiratory therapy device 122, (ii) the conduit 126, (iii) a connector between components of the respiratory therapy system 120, (iv) the user interface 124, (v) a headgear (e.g., straps) associated with the user interface, or (vi) a combination thereof. In some implementations, the microphone 140 is in fluid communication with the airflow pathway (e.g., an airflow pathway between the flow generator/motor and the distal end of the conduit). By fluid communication, it is intended to also include configurations wherein the microphone is in acoustic communication with the airflow pathway without necessarily being in direct or physical contact with the airflow. For example, in some implementations, the microphone is positioned on a circuit board and in fluid communication, optionally via a duct sealed by a membrane, to the airflow pathway.

In some implementations, one or more secondary sensors may be used in addition to the primary sensor to generate additional data. In some such implementations, the one or more secondary sensors include: a microphone (e.g., the microphone 140 of the system 100), a flow rate sensor (e.g., the flow rate sensor 134 of the system 100), a pressure sensor (e.g., the pressure sensor 132 of the system 100), a temperature sensor (e.g., the temperature sensor 136 of the system 100), a camera (e.g., the camera 150 of the system 100), a vane sensor (VAF), a hot wire sensor (MAF), a cold wire sensor, a laminar flow sensor, an ultrasonic sensor, an inertial sensor, or a combination thereof.

Additionally, or alternatively, one or more microphones (the same as, or similar to, the microphone 140 of FIG. 1) can be integrated in and/or coupled to a co-located smart device, such as the user device 170, a TV, a watch (e.g., a mechanical watch or another smart device worn by the user), a pendant, the mattress 232, the bed 230, beddings positioned on the bed 230, the pillow, a speaker (e.g., the speaker 142 of FIG. 1), a radio, a tablet device, a waterless humidifier, or a combination thereof. A co-located smart device can be any smart device that is within range for detecting sounds emitted by the user, the respiratory therapy system 120, and/or any portion of the system 100. In some implementations, the co-located smart device is a smart device that is in the same room as the user during the sleep session.

Additionally, or alternatively, in some implementations, one or more microphones (the same as, or similar to, the microphone 140 of FIG. 1) can be remote from the system 100 (FIG. 1) and/or the user 210 (FIG. 2), so long as there is an air passage allowing acoustic signals to travel to the one or more microphones. For example, the one or more microphones can be in a different room from the room containing the system 100.

As used herein, a sleep session can be defined in multiple ways. For example, a sleep session can be defined by an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Generally, the sleep session includes any point in time after the user 210 has laid or sat down in the bed 230 (or another area or object on which they intend to sleep), and has turned on the respiratory therapy device 122 and donned the user interface 124. The sleep session can thus include time periods (i) when the user 210 is using the CPAP system but before the user 210 attempts to fall asleep (for example when the user 210 lays in the bed 230 reading a book); (ii) when the user 210 begins trying to fall asleep but is still awake; (iii) when the user 210 is in a light sleep (also referred to as stage 1 and stage 2 of non-rapid eye movement (NREM) sleep); (iv) when the user 210 is in a deep sleep (also referred to as slow-wave sleep, SWS, or stage 3 of NREM sleep); (v) when the user 210 is in rapid eye movement (REM) sleep; (vi) when the user 210 is periodically awake between light sleep, deep sleep, or REM sleep; or (vii) when the user 210 wakes up and does not fall back asleep.

The sleep session is generally defined as ending once the user 210 removes the user interface 124, turns off the respiratory therapy device 122, and gets out of bed 230. In some implementations, the sleep session can include additional periods of time, or can be limited to only some of the above-disclosed time periods. For example, the sleep session can be defined to encompass a period of time beginning when the respiratory therapy device 122 begins supplying the pressurized air to the airway or the user 210, ending when the respiratory therapy device 122 stops supplying the pressurized air to the airway of the user 210, and including some or all of the time points in between, when the user 210 is asleep or awake.

For example, the user interface being characterized may include "direct category" user interfaces, "indirect category" user interfaces, direct/indirect headgear, direct/indirect conduit, or the like, such as the example types described with reference to FIGS. 3A-3B, 4A-4B, and 5A-5B. As another example, the user interface being characterized may include the following: AcuCare™ F1-0 non-vented (NV) full face mask, AcuCare™ F1-1 non-vented (NV) full face mask with AAV, AcuCare™ F1-4 vented full face mask, AcuCare™ high flow nasal cannula (HFNC), AirFit™ F10, AirFit™ F20, AirFit™ F30, AirFit™ F30i, AirFit™ masks for AirMini™, AirFit™ N10, AirFit™ N20, AirFit™ N30, AirFit™ N30i, AirFit™ P10, AirFit™ P30i, AirTouch™ F20, AirTouch™ N20, Mirage Activa™, Mirage Activa™ LT, Mirage™ FX, Mirage Kidsta™, Mirage Liberty™, Mirage Micro™, Mirage Micro™ for Kids, Mirage Quattro™, Mirage SoftGel™ Mirage Swift™ II, Mirage Vista™, Pixi™, Quattro™ Air, Quattro™ Air NV, Quattro™ FX, Quattro™ FX NV, ResMed® full face hospital mask, ResMed® full face hospital NV (non-vented) mask, ResMed® hospital nasal mask, Swift™ FX, Swift™ FX Bella, Swift™ FX Nano, Swift™ LT, Ultra Mirage™, Ultra Mirage™ II, Ultra Mirage™ NV (non-vented) full face mask, Ultra Mirage™ NV (non-vented) nasal mask, or any combination thereof.

In some implementations, a remaining useful life of an interface (e.g., the user interface 124 or the examples shown in FIGS. 3A-5B) of a respiratory therapy system (e.g., the respiratory therapy system 120) can be determined. First, acoustic data associated with an acoustic reflection of an acoustic signal is received. The acoustic reflection is indicative of a portion of a structural shape of the interface. As disclosed above, the acoustic signal may be generated or emitted at a predetermined interval by a speaker of the respiratory therapy system, such as the speaker 142.

The received acoustic data is analyzed to identify a physical feature 352 (FIG. 3B) of the portion of the structural shape of the interface. For example, in some implementations, the physical feature includes a hole in the interface, and the hole progressively expands over time based on usage. Additionally or alternatively, in some implementations, the physical feature includes a fin on the interface, and the fin progressively dissolves over time based on usage. In some such implementations, the fin is integral with the interface. In some other such implementations, the fin is separate and distinct from the interface and coupled thereto. In some implementations, the fin has a geometrical shape, which has an edge that has a dimension that shortens over time indicating the remaining useful life.

The physical feature is then compared to a reference feature. In some implementations, the comparing includes determining a value associated with the physical feature and comparing the value with a reference value associated with the reference feature. In an example where the physical feature is a hole in the user interface, the reference feature refers to the hole in the user interface that is not yet put into use by the user. The initial dimension of the hole may be measured, for example, by the acoustic technique as discussed above at the time when the user first puts on the user interface. Thus, the initial dimension of the hole will be used as the reference value. In an alternative example, a user interface that is provided with the physical feature (e.g., a hole in the user interface, a fin on the user interface or other suitable physical feature) may be provided with a specific model number. In such a case, the initial dimension of the physical feature may be measured at the time of introducing the physical feature to the user interface in the manufacturing process and the measurement will be recorded and associated with the specific model number. Thus, the reference value may be extracted when the RPT device first detects the physical feature or when the user manually inputs the specific model number of the user interface when prompted by the RPT device 122. Although the examples illustrated were referring to either a hole or a fin, it is understood that the same or similar techniques as described may be applied to obtain the reference value of any other suitable physical feature that is introduced on the user interface.

Based at least in part on the comparison, the remaining useful life of the interface is determined. For example, in some implementations, the remaining useful life of the interface is a function of usage by a user of the interface. Additionally, in some implementations, the remaining useful life of the interface is further the function of a manufacturing date of the interface.

In some implementations, the remaining useful life of the user interface may be presented to the user through the display device 172 of the user device 170, the display device 128 of the RPT device 122, or both. A reminder or a notification may be sent to the user and presented through the display device 172 of the user device or the display device 128 of the RPT device 122 when the remaining user life is less than a threshold value (e.g., less than 15 days). The user may also be presented with an option to purchase a new user interface through the display device 172 of the user device 170, the display device 128 of the RPT device 122, or both upon receipt of the reminder or notification.

Although the acoustic technique has been described to measure the change of the physical feature (e.g., hole expansion or fin dissolves over time) on the user interface, other suitable techniques (e.g., camera) may be employed. One or more elements or aspects or steps, or any portion(s) thereof, from one or more of any of claims below can be combined with one or more elements or aspects or steps, or any portion(s) thereof, from one or more of any of the other claims or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method for determining a remaining useful life of an interface of a respiratory therapy system, the method comprising:

receiving, via a microphone of the respiratory therapy system, acoustic data associated with an acoustic reflection of an acoustic signal, the acoustic reflection being indicative of a portion of a structural shape of the interface, wherein the acoustic signal is emitted by a speaker of the respiratory therapy system, and wherein the acoustic reflection is a reflection of the acoustic signal off the portion of the structural shape of the interface;

analyzing the received acoustic data to identify a physical feature of the portion of the structural shape of the interface;

comparing the physical feature to a reference feature; and based at least in part on the comparison, determining the remaining useful life of the interface.

2. The method of claim 1, wherein the physical feature includes a hole in the interface, and the hole progressively expands over time based on usage.

3. The method of claim 1, wherein the physical feature includes a fin on the interface, and the fin progressively dissolves over time based on usage.

4. The method of claim 3, wherein the fin is integral with the interface.

5. The method of claim 3, wherein the fin is separate and distinct from the interface and coupled thereto.

6. The method of claim 3, wherein the fin has a geometrical shape.

7. The method of claim 6, wherein the shape has an edge that has a dimension that shortens over time indicating the remaining useful life.

8. The method of claim 1, wherein the acoustic signal is generated or emitted at a predetermined interval by a speaker of the respiratory therapy system.

9. The method of claim 1, wherein the remaining useful life of the interface is a function of usage by a user of the interface.

10. The method of claim 9, wherein the remaining useful life of the interface is further the function of a manufacturing date of the interface.

11. The method of claim 1, wherein the comparing includes determining a value associated with the physical feature and comparing the value with a reference value associated with the reference feature.

12. The method of claim 1, further comprising presenting the remaining useful life of the interface on a display device of (i) a user device, (ii) a respiratory pressure therapy device, or (iii) both.

13. A system comprising:

a control system comprising one or more processors; and a memory having stored thereon machine readable instructions;

wherein the control system is coupled to the memory, and the method of claim 1 is implemented when the machine executable instructions in the memory are executed by at least one of the one or more processors of the control system.

14. A system for determining a remaining useful life of an interface of a respiratory therapy system, the system comprising a control system configured to implement the method of claim 1.

15. A non-transitory computer readable medium comprising instructions which, when executed by a computer, cause the computer to carry out the method of claim 1.

16. The method of claim 1, wherein a dimension of the physical feature progressively changes over time based on usage of the user interface, wherein the reference feature correspond to an initial dimension of the physical feature, and wherein the comparing the physical feature to the reference feature includes determining a current dimension of the physical feature and comparing the current dimension of the physical feature to the initial dimension of the physical feature.

* * * * *